United States Patent [19]
Gutierrez Rigo

[11] Patent Number: 5,229,119
[45] Date of Patent: Jul. 20, 1993

[54] PHARMACEUTICAL COMPOSITION AND METHOD OF TREATMENT UTILIZING THE COMPOSITION

[75] Inventor: Avelino Gutierrez Rigo, Tijuana, Mexico

[73] Assignee: Angela Gutierrez Rigo, Col. Nativitas, Mexico

[21] Appl. No.: 780,877

[22] Filed: Oct. 18, 1991

[51] Int. Cl.$^5$ ............................................. A61K 35/78
[52] U.S. Cl. ................................................ 424/195.1
[58] Field of Search ................................... 424/195.1

[56] References Cited

U.S. PATENT DOCUMENTS 4,124,724 11/1978 Agoro .................................. 424/317
4,568,546 2/1986 Vicario-Arcos ................. 424/195.1

OTHER PUBLICATIONS

B. S. Vishwanath et al., *Toxicon* 25:929–937 (1987).
W. B. Mors et al., *Toxicon* 27:1003–1009 (1989).

*Primary Examiner*—John W. Rollins
*Attorney, Agent, or Firm*—Merchant, Gould, Smith, Edell, Welter & Schmidt

[57] ABSTRACT

An anti-venom composition comprising extracts of active components of the plants *Abelmoscus moschatus* and *Mikania guaco* combined at effective ratios; the method of preparing this composition; the pharmaceutical products derived of said extracts of active components; and a method of treating snakebites, scorpion stinging and the like using said composition.

9 Claims, No Drawings

PHARMACEUTICAL COMPOSITION AND METHOD OF TREATMENT UTILIZING THE COMPOSITION

FIELD OF THE INVENTION

The present invention refers to a anti-venom composition comprising highly concentrated extracts of active components of the plants *Abelmoscus moschatus* and *Mikania guaco* combined at effective ratios; the method of preparing the composition; the pharmaceutical products derived of said extracts of active components; and the method of use of said composition for treating snakebites, scorpion stingings and the like.

BACKGROUND OF THE INVENTION

Currently available methods of treating bites or stingings of poisonous animals go from the most rudimentary, as making a rush incision and prompt suction of lethal amounts of the venom inoculated, up to those more sophisticated methods, as administering previous prepared serum, which usually is specific to the venom under consideration.

The above referred type of serums are generally prepared by injecting the venom of a given snake, for example, into horses and extracting the anti-venom produced therefrom from the horse serum.

One of the several disadvantages of this kind of anti-venoms is that said serum may be highly toxic to people who suffer from allergy against the antibodies contained by this serum.

Other drawback of these kind of anti-venoms consists on the fact that serums prepared according to the above referred method are usually very specific, that is to say, they are useful only against the particular venom from which said serum was developed and generally not against any other venom.

Besides, administration of these serums must always be by intravenous trip, which makes more difficult its use when there is nobody with the needed skills to administer the anti-venom serum to the victim of the snakebite or scorpion stinging, for example.

Due to the above, the field of application of said anti-venoms has been considerably restricted in view of the fact that, on one hand, certain persons do not accept the serum and some times they die, if not of the venom injected by the animal, by the allergic shock caused by the serum itself; and, on the other hand, due to its specificity and the knowledge and skills needed to administer the serum.

Seeking solutions to drawbacks showed by the above referred anti-venoms a wide variety of compositions of natural origin has been formulated as attempts to prevent fatalities when persons suffer the bite or stinging of a venomous animal such as snakes, scorpions and the like.

U.S. Pat. No. 4,568,546 issued to Vicario-Arcos on Feb. 4, 1986 teaches an anti-venom composition comprising an ethyl alcohol infusion of plants red cinchona, curcuma root, aloes, saffron, white agaric, nutmeg, manna, gencian, orange blossom, fhubarb and cinnamon, together with an amount of iron filings.

U.S. Pat. No. 4,124,724 issued to J. W. Agoro on Nov. 7, 1978 discloses the use of active factors in the roots of the plants *Berkheya spekeana* and *Echinops amplexicaulis*, namely crystalline caffeic acid derivatives, as anti-snake venom.

An important point to be considered in compositions of natural origin is the content of other materials usually accompanying active components and which materials may have side effects on victims of poisonous animals.

According to the present invention a pharmaceutical composition of natural origin has been developed. This composition does not exhibit side effects derived from materials other than the active components of the plants from which the composition is obtained.

Also this pharmaceutical composition is not limited by any reduced specificity but it is applicable to a wide variety of venoms produced by poisonous animals.

It is an object of the present invention to provide a composition comprising extracts of active components of plants *Abelmoscus moschatus* and *Mikania guaco*, useful against venoms of poisonous animals.

It is one another object of the present invention to provide a pharmaceutical composition of natural origin which does not produce any allergic shock derived from others components of plants used, and which is very effective against the effects of venoms when administered at pharmaceutically acceptable ratios to victims of poisonous animals.

Even another object of the present invention is to provide a composition of strict natural origin having not antibodies which may cause lateral reactions when said composition is given to victims of poisonous animals.

Still another object of the present invention is to provide a composition suitable to be administered orally and which is quickly assimilated by mammalian organisms to develop its action against activity of venoms of poisonous animals.

Another object of the present invention is to provide a composition of pharmaceutical products comprised in extracts of active components of plants *Abelmoscus moschatus* and *Mikania guaco*, which make possible to be combined at effective ratios without developing lateral reactions when said composition is used to treat victims of bites or stingings of venomous animals.

An additional object of the present invention is to provide a method of treating mammalians with the above composition so that lethal effects of venous inoculated by snakes, scorpions and the like can be anulled.

These objects and others ancilliary thereto are preferably accomplished as follows:

DETAILED DESCRIPTION

The present invention provides a composition of extracts of active components of the plants *Abelmoscus moschatus* and *Mikania guaco* combined at effective ratios and which is preferably obtained by liquid-solid extraction methods with suitable solvents as ether, alcohol and water.

Each of the above referred extracts is obtained by methods independent one of each other. Then said extracts are combined at effective ratios in order to obtain a pharmaceutical composition comprising effective amounts of active components suitable to be administered through the oral route.

According to a highly preferred embodiment of this invention the method of preparation of the composition is as follows:

On one hand, seeds, leaves and/or stems of *Abelmoscus moschatus* plant are crushed and submerged in a suitable solvent as, for example, ethyl alcohol. Extraction of active components is accelerated by vigorous stirring the mixture for a certain period of time after which the liquid is filtered through conventional methods.

On the other hand, stems, leaves and/or roots of *Mikania guaco* plant are properly crushed and submerged in water, preferably purified water. The temperature of the mixture is increased up to the boiling point and it is kept at said point during the time needed to extract the active components; after said time heating is suspended and the mixture is taken up to room temperature. The liquid is filtered and the solid is discarded.

Once prepared, the above extracts are combined at effective ratios bearing in mind the grading of the resulting composition in terms of Gay Lussac grades of alcohol.

The term "effective ratios" means all those ratios at which active components of plants *Abelmoscus moschatus* and *Mikania guaco* plants provided by extracts are sufficient to annul lethal effects of venoms produced and inoculated by poisonous animals to mammalians.

The term "active components" means all those components of the plants *Abelmoscus moschatus* and *Mikania guaco* whose activity in mammaliam organisms nullifies lethal activity of venoms inoculated to said organisms by poisonous animals.

The alcoholic-aqueous pharmaceutical composition prepared according to the above technique has been found to be absolutely effective against venom of poisonous animals as, for example, nauyaque snake (Botrops atrox) and rattlesnake (Crotalus durissus terrificus), scorpions, spiders, vesps and bees.

Other advantages of the pharmaceutical composition of the present invention are: it is not required refrigeration to keep the activity and effectiveness of this composition, it is administered through the oral route, it has no lateral effects, its action is faster than that of antivenom serums, its effectiveness is not limited to a particular venom of poisonous animals, and it has no caducity.

The recommended dose is a function of weight of victim, preferably it is recommended to give two doses of 10 to 35 ml, separated by 5 minutes one from each other.

The present invention will be more fully understood by means of the following examples which are given as illustrative but not as limitative of the scope of the invention.

EXAMPLE 1

An extract of active components was prepared by grinding 1,000 g of seeds of *Abelmoscus moschatus* plant in a manual mill up to obtaining a powder of substantially the same size of grain, approximately 2 mm. The powder was added to a five-liter container provided with stirring means and having 3,000 ml of ethyl alcohol, 96 degrees of purity. The mixture was put under an strong and continuous stirring for approximately 60 minutes at 10–30 centigrades degrees. The solid residue was separated apart from the liquid by conventionals techniques of filtration. The liquid obtained was divided into two portions which were marked each as first extract and were allowed to stand during 12 hours at room temperature.

EXAMPLE 2

An extract of active components was prepared by crushing 50 g of steam of *Mikania guaco* plant in an electric mill up to obtaining a substantially pulverulent material. The powder was added to a two-liter container provided with stirring and heating means and having 1,250 ml of drinkable water. The mixture was homogenized and put under continuous stirring, the temperature was increased up to the boiling point and the mixture was kept for 90 minutes under said temperature after which said mixture was allowed to cool up to room temperature. The solid residue was separated apart from the liquid by centrifugation and the liquid obtained was divided into two portions which were marked each as second extract.

EXAMPLE 3

A pharmaceutical composition of extracts of active components of the plants *Abelmoscus moschatus* and *Mikania guaco* was prepared by combining effective amounts of the above first and second extracts as follows: portions of the first and second extracts were taken and combined by mixing two parts of the first extract with one part of the second extract. Care was taken to assure that grading of the resulting composition was of 25 Gay Lussac grades at 15 centigrade degrees.

EXAMPLE 4

Four dogs received nauyaque snake venom and three were treated as follows:
First dog: male, black color, weighing approximately 15 Kg, not visible symptoms of illness, age two years.
Second dog: male, white color, weighing approximately 12 Kg, not visible symptoms of illness, age two years.
Third dog: male, yellow color, weighing approximately 14 Kg, not visible symptoms of illness, age two years.
Fourth dog: male, brown color, weighing approximately 14 Kg, not visible symptoms of illness, age two and a half years.

An sterile suspension of nauyaque snake venom was prepared in chemically pure and neutral glycerin during three days in stove at 37 centigrade degrees.

14:00 hrs., each of the above dogs was subcutaneously injected on the left-hand rear member an amount of venom enough to kill in 22 hours (hrs.) 25 Kg of live canine weight, at a rate of 4 mg of venom per Kg.

14:15 hrs., to the first dog was given through the oral route 20 ml of extract prepared according to the Example 1; to the second dog was given through the oral route 20 ml of extract prepared according to the Example 2; to the third dog was given 20 ml of the composition prepared according to the Example 3; and the fourth dog received no venom and was taken as the control dog.

For briefness symptoms and behavior of the first dog will only be given in this Example. Initial local symptoms, intense pain at the left-hand rear member; ptialism, which ceased half an hour after the administration of the extract. 14:30 hrs., temperature 39.8 centigrade degrees (c.d.), pulse 14, breathing 25; vomiting of the contents of the stomach, moans. 18:00 hrs., dog in calm, temperature decreased to 39 c.d., pulse 12, breathing 18. 8:00 hrs. of the following day, the dog was intramuscularly injected 2 ml of extract prepared according to the Example 1 but using ether instead of alcohol. 11:00 hrs., temperature 39 c.d., pulse 11, breathing 16. The swelling of the left-hand rear member had enlarged to a great extend and the inner face showed a cyanotic aspect. 13:00 hrs., temperature 24.4 c.d., breathing 32, pulse 11, the dog moans and shows the tongue at intervals, which appears flawy. 13:30 hrs., the inner face of the left-hand rear member drains off an odorless, mucous consistence, wine color liquid. 14:00 hrs., the dog is taken to a clean well ventilated cage and was administered nothing else. After five days the dog was completely healthy.

The third dog was completely healthy after the third day of administration of the anti-venom composition. The second and fourth dogs died, the second 28 hours after the injection of the venom and the fourth 22 hours after the injection of the venom.

EXAMPLE 5

Following the techniques of Examples 1 through 4 thirty further tests were run. The following results were obtained: one dog out of ten dogs treated with an aqueous extract prepared according to the Example 2 survived to the injection of the venom and recovered its healthy condition. Three dogs out of ten dogs treated with an ethereal extract prepared according to the Example 1 survived to the injection of the venom and recovered their healthy condition. These aqueous and ethereal extracts were intramuscularly administered to the dogs. Ten dogs out of ten dogs treated with an hydro-alcoholic extract prepared according to the Example 3 and administered to the dogs through the oral route survived to the injection of the venom and recovered their healthy condition.

EXAMPLE 6

Narration of a real experience of the inventor.

In an attempt to obtain serpent's fresh venom the inventor went to the natural habitat of nauyaque snakes. First day of the searching, approximately at 10:00 hrs. the inventor is making way on the grass and suffered a nauyaque snakebite on the last interphalanges joint of the right-hand pinky. After searching among plants an approximately 1.50-mt long nauyaque snake (Botrops atrox) was found curled on surrounding bushes. A tight tourniquet was placed on the inventor's right-hand wrist. Since the beginning pain was intense and in a few minutes it spread out to the full arm and the right-hand leg. 10 minutes after the bite, vomiting started accompanied with abundant secretion of bloody saliva. Urinate and defecate desired appeared. A general weakness accompanied with abundant sweating and uncontrollable tremor overwhelmed the inventor. 45 minutes after the bite the inventor was given through the oral route 20 ml of hydro-alcoholic composition substantially prepared according to the Example 3, which composition was vomited almost immediately. A second 20 ml dose of the above composition was given to the inventor and the tourniquet was removed. Weakness and ears ringing persisted. Vomiting and sweating ceased. The inventor remained sleeping up to the 22:00 hours time in which he was waked up and a 10 ml dose of the above referred extract was given through the oral route. Weakness persisted but a perfect conscious state existed while in vigil. At 14:00 hrs. of the second day the inventor was hungry and ate tea and boiled potatoes with no further doses of the above composition. 10 days after the snakebite recovery of inventor was full and complete.

Although certain specific embodiments of the present invention have been shown and described, it is to be understood that other modifications thereof are possible without separating of the essence and scope of the invention. This invention, therefore, is not to be restricted except insofar as is necessitated by the prior art and by the spirit of the appended claims.

What is claimed is:

1. A composition, comprising: an extract derived from the plant *Abelmoscus moschatus* and an extract derived from the plant *Mikania guaco*, the extracts being combined with a compatible carrier, the extracts comprising active components effective to inhibit the lethal effects of a venom of a poisonous animal in a mammal.

2. A pharmaceutical composition, comprising:
   an extract derived from the plant *Abelmoscus moschatus* and an extract derived from the plant *Mikania guaco*, the extracts comprising active components capable of inhibiting the lethal effects of a venom of a poisonous animal, the extracts being combined with a pharmaceutically-acceptable carrier and combined together in a ratio effective to inhibit the lethal effects of the venom in a mammal.

3. The pharmaceutical composition of claim 2, wherein the extracts are derived from seeds of the *Abelmoscus moschatus* plant and a stem of the *Mikania guaco* plant.

4. The pharmaceutical composition of claim 3, wherein the carriers are selected from the group consisting of alcoholic, ethereal and aqueous carriers.

5. The pharmaceutical composition of claim 4, wherein the extracts are combined in a ratio of about 1:0.3 to 1:0.8 of *Abelmoscus moschatus* extract to *Mikania guaco* extract.

6. The pharmaceutical composition of claim 5, wherein the extract of the *Abelmoscus moschatus* plant is an alcoholic extract and the extract of the *Mikania guaco* plant is an aqueous extract, the extracts being combined in a ratio of about 1:0.5 of *Abelmoscus moschatus* extract to *Mikania guaco* extract.

7. The pharmaceutical composition according to claim 6, wherein the composition is in a form suitable for oral administration to the mammal.

8. A method of preparing a composition effective to inhibit lethal effects of a venom of a poisonous animal in a mammal, which method comprises:
   a) providing an extract of an *Abelmoscus moschatus* plant by combining seeds, leaves or stems of the plant with an alcoholic solvent for a time effective to extract active components from the plant, the active components having activity against the lethal effects of the venom of the poisonous animal;
   b) providing an extract of a *Mikania guaco* plant by combining seeds, leaves or roots of the plant with an aqueous solvent and heating the aqueous solvent and plant parts to boiling for a time effective to extract active components from the plant parts, the active components having activity against the lethal effects of the venom of the poisonous animal; and
   c) combining the extracts of steps a) and b) in a ratio of about 1:0.3 to 1:0.8 of extract a) to extract b).

9. A method of treating a mammalian victim of a poisonous animal to inhibit lethal effects of a venom of said poisonous animal in the mammalian victim, which method comprises orally administering an effective dose of a pharmaceutical composition comprising an extract of an *Abelmoscus moschatus* plant in an alcoholic carrier and an extract of a Mikania guaco plant in an aqueous carrier; the extracts comprising components from the plants having activity against the lethal effects of the venom; the extracts being combined at a ratio of about 1:0.5 of *Abelmoscus moschatus* extract to *Mikania guaco* extract.

* * * * *